United States Patent [19]
Flora et al.

[11] 4,269,828
[45] May 26, 1981

[54] INDOLE ANTI-INFLAMMATORY COMPOSITION

[75] Inventors: Lawrence Flora, Hamilton; Marion D. Francis, Cincinnati, both of Ohio

[73] Assignee: The Procter & Gamble Company, Cincinnati, Ohio

[21] Appl. No.: 924,477

[22] Filed: Jul. 13, 1978

Related U.S. Application Data

[63] Continuation of Ser. No. 782,144, Mar. 28, 1977, abandoned.

[51] Int. Cl.³ .................... A61U 31/40; A61U 31/66
[52] U.S. Cl. .................................... 424/204; 424/274
[58] Field of Search ...................... 424/204, 222, 274

[56] References Cited

U.S. PATENT DOCUMENTS

| | | | |
|---|---|---|---|
| 3,553,314 | 6/1971 | Francis | 424/204 |
| 3,553,315 | 6/1971 | Francis | 424/204 |
| 3,584,124 | 6/1971 | Francis | 424/204 |
| 3,584,125 | 6/1971 | Francis | 424/204 |
| 3,641,246 | 2/1972 | Francis | 424/204 |
| 3,662,066 | 5/1972 | Francis | 424/204 |
| 3,678,164 | 7/1972 | Francis | 424/204 |
| 3,683,080 | 8/1972 | Francis | 424/204 |
| 4,044,125 | 8/1977 | Wallsling | 424/233 |
| 4,049,803 | 9/1977 | Cotly et al. | 424/233 |

*Primary Examiner*—Stanley J. Friedman
*Attorney, Agent, or Firm*—Steven J. Goldstein; Michael J. Roth; Richard C. Witte

[57] ABSTRACT

The anti-inflammatory activity of indomethacin, indoxole, and other indole-based drugs is enhanced by administration thereof in conjunction with a phosphonate compound such as EHDP or $Cl_2MDP$.

10 Claims, No Drawings

INDOLE ANTI-INFLAMMATORY COMPOSITION

This is a continuation of application Ser. No. 782,144, filed Mar. 28, 1977, now abandoned.

BACKGROUND OF THE INVENTION

The present invention relates to compositions and processes for relieving inflammation. More specifically, phosphonate compounds are administered in conjunction with well-recognized, indole-based, anti-inflammatory agents such as indomethacin, indoxole, and the like, to treat undesirable inflammation of body tissues.

Inflammation, or the "inflammatory response", is the result of complex interconnected physiological events, including increased vascular permeability, fluid accumulation, and the migration of a changing population of inflammatory cells into the inflamed area. The clinical manifestations of inflammation include swelling (edema), increased local temperature, erythema, and pain. The inflammatory response can be triggered by any of a number of causative factors, including certain bacteria, radiation, hypersensitivity to chemical agents, arthritis-like conditions, and the like. The inflammatory response is generally believed to be a primary defense mechanism in the body, but, unchecked, can become excessive and can result in functional impairment.

The use of indole compounds, especially indomethacin and indoxole, to combat inflammation and attendant pain is accepted medical practice. The indole agents are commonly employed to relieve pain and inflammation associated with, for example, arthritis, bursitis, and the like.

The use of pharmacologically-active phosphonate compounds to check the anomalous mobilization and deposition of calcium phosphate salts in the body, e.g., as a treatment for arthritis, is known.

By the present invention, pharmacologically active phosphonate compounds are administered in conjunction with indole-based anti-inflammatory agents to provide an improved therapy for inflammation, especially in the treatment of arthritis, and like diseases.

RELATED REFERENCES

The indoles are known for use in the treatment of rheumatic and arthritic disorders; Thompson, et al., *Br. Med. J.* i/1966, 80; Hart, et al., *Br. Med. J.* ii/1963, 965; Kelly, *J. Am. Geriat. Soc.*, 1966, 14, 48; O'Brien, *Clin Pharmac. Ther.*, 1968, 9, 94 (review article).

Analgesic abuse is often noted in patients with chronic gastrointestinal or renal disease. Many such patients are in the habit of taking analgesics for prolonged periods and usually in excessive doses. *Clin. Med.*, 1968, 75 (Aug.) 19; *Lancet* ii/1969, 1233. A listing of references relating to indole analgesics and contraindications appears in Martindale, THE EXTRA PHARMACOPOEIA, 26th Ed., The Pharmaceutical Press, London, pp. 238–239.

The phosphonate compounds used in the practice of this invention are reported in the literature as being useful in the treatment of anomalous mobilization and deposition of calcium phosphate salts (bone mineral) in humans and other animals. See especially the U.S. Patents of M. D. Francis: Nos. 3,683,080, granted Aug. 8, 1972; 3,678,164, granted July 18, 1972; 3,662,066, granted May 9, 1972; 3,553,314, granted Jan. 5, 1971; 3,553,315, granted Jan. 5, 1971; 3,584,124, granted June 8, 1971; 3,584,125, granted June 8, 1971; and 3,641,246, granted Feb. 8, 1972.

The article by Francis, Flora and King, entitled "The Effects of Disodium Ethane-1-Hydroxy-1,1-Diphosphonate on Adjuvant Induced Arthritis in Rats", appearing in *Calc. Tiss. Res.* 9, 109–121 (1972) mentions the use of phosphonates to inhibit inflammatory erosion of cartilage in rats.

The copending application of L. Flora, entitled PHARMACEUTICAL COMPOSITION, Ser. No. 705,650, filed July 15, 1976, discloses the topical administration of phosphonate compounds of the type used herein to humans to alleviate pathological calcification.

By the present invention, the anti-inflammatory activity of indole compounds is potentiated by phosphonate compounds. Thus, the invention encompasses a means whereby a patient afflicted with tissue inflammation can secure relief without risking analgesic abuse due to over-use of indole-based anti-inflammatories.

SUMMARY OF THE INVENTION

The present invention encompasses compositions and means for treating pain and inflammation in animal tissues, especially in humans. The invention provides effective drug combination compositions and therapy, and is based on the use of pharmacologically-active phosphonate compounds in combination with indole-based anti-inflammatory agents such as indomethacin, indoxole, and the like.

The compositions of this invention comprise an effective amount of an indole-based anti-inflammatory compound in combination with an effective amount of a phosphonate compound. The compounds act in concert to provide improved anti-inflammatory benefits.

The invention also encompasses treatment regimens comprising administering an effective amount of the indole-based anti-inflammatory agent and an effective amount of a phosphonate compound to an animal, especially a human, suffering from tissue inflammation.

Preferred indole-based treatment regimens and compositions herein employ a member selected from the group consisting of indomethacin, indoxole, and the pharmaceutically-acceptable salts and esters thereof, or mixtures thereof, and, as the phosphonate compound, a member selected from the group consisting of ethane-1-hydroxy-1,1-diphosphonic acid, and the pharmaceutically-acceptable salts and esters thereof, and dichloromethanediphosphonic acid, and the pharmaceutically-acceptable salts and esters thereof. The dichloromethanediphosphonates are surprisingly effective at low usage levels, and are especially preferred herein. Mixtures of indole-based anti-inflammatory agents can be used, as can mixtures of phosphonates.

DETAILED DESCRIPTION OF THE INVENTION

The compositions and treatment regimens of this invention employ: (1) a safe and effective amount of a pharmaceutically-acceptable indole-based anti-inflammatory compound; and (2) a safe and effective amount of a pharmaceutically-acceptable phosphonate compound. These compounds are administered to alleviate inflammation in a patient in need of such treatment.

By "safe and effective amount of infole-based anti-inflammatory compound" herein is meant sufficient indole compound to alleviate tissue inflammation, at a reasonable benefit/risk ratio attendant with any medical treatment, when used in the manner of this invention.

Within the scope of sound medical judgment, the dosage of indole compound will vary with the particular condition being treated, the severity of the condition, the duration of the treatment, and the specific indole and phosphonate compounds employed.

By "safe and effective amount of phosphonate compound" herein is meant a sufficient amount of the phosphonate compound to potentiate the anti-inflammatory response over that elicited by the indole compound, alone, at a reasonable benefit/risk ratio attendant with any medical treatment. Within the scope of sound medical judgment, the dosage of phosphonate will vary with the particular condition being treated, the severity of the condition, the duration of the treatment, and the specific phosphonate and indole compounds employed.

By "pharmaceutically-acceptable" herein is meant that the drug compounds and other ingredients used in the present compositions and processes are suitable for use in contact with the tissues of humans and lower animals without undue toxicity, irritation, allergic response, and the like, commensurate with a reasonable benefit/risk ratio.

The term "administration" of the compounds and compositions herein includes systemic use, as by injection (especially parenterally), intravenous infusion, suppositories and oral administration thereof, as well as topical application of the compounds and compositions to the afflicted situs.

By "topical application" herein is meant directly laying on or spreading the compounds and compositions on epidermal tissue (including outer skin and oral, gingival, nasal, etc., tissue).

By "afflicted situs" herein is meant a localized area of inflammation, and the immediate surrounding area.

The process of the present invention is most conveniently carried out by administering compositions comprising both a phosphonate compound and a compatible indole compound and, optionally, compatible carrier materials.

By the term "comprising" as used herein is meant that various other, compatible drugs and medicaments, as well as inert ingredients, can be conjointly employed in the compositions and processes of this invention, as long as the critical phosphonate compounds and indole-based anti-inflammatory compounds are used in the manner disclosed. The term "comprising" thus encompasses and includes the more restrictive terms "consisting of" and "consisting essentially of" which characterize the use of the essential phosphonate compounds and indole compounds.

By "compatible" herein is meant that the components of the compositions are capable of being commingled without interacting in a manner which would substantially decrease the efficacy of the total compositions under ordinary use situations.

By "carrier" herein is meant a liquid, fluid or solid material which can optionally be used to provide finished compositions for systemic or topical administration of the drug compounds.

All percentages herein are by weight, unless otherwise specified.

The phosphonate compounds and indole compounds critical to the practice of this invention are described more fully hereinafter. Optional ingredients which can be included in the compositions to provide aesthetic, cosmetic, and convenience benefits, but which are not critical to the practice of the invention, are also disclosed.

The indole-based compounds used herein comprise derivatives of indole, which is represented by the formula

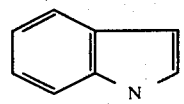

As is well known in the art, indole can be derivatized at the nitrogen atom or on the ring system to provide various pharmacologically-active indole-based compounds which exhibit analgesic and/or anti-inflammatory activity. The indole-based compounds employed in the practice of this invention are all well known in the medical arts and their anti-inflammatory activity in humans and lower animals is well documented.

Anti-inflammatory indole compounds, their pharmaceutically-acceptable salts, and their pharmaceutically-acceptable esters are used herein. Such materials include, for example, indomethacin, which is represented by the formula

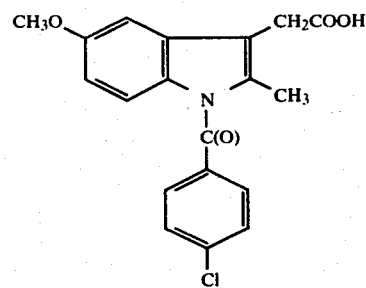

and indoxole, which is represented by the formula

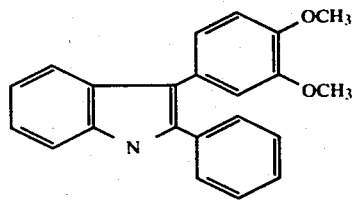

The foregoing indole-based compounds are preferred for use herein. However, as is well known in the art, there are a variety of other indole-based anti-inflammatory agents which are prepared by modifying the substituent groupings, for example on the rings. One of the more complete listings of such materials, references to their mode of preparation and their therapeutic uses as anti-inflammatory agents appears in the text ANTIINFLAMMATORY AGENTS Chemistry and Pharmacology, Vol. I, Scherrer & Whitehouse, Academic Press, New York, pp. 107–110 and 184–186 (1974), the disclosures of which are incorporated herein by reference. Such indole-based compounds can also be used herein.

The organophosphonate compounds (or, more succinctly, "phosphonates") employed in the manner of this invention are of the following type.

The phosphonate compounds which can be employed in the present invention are characterized by the phosphonate moiety ($-PO_3M_2$, wherein M represents H or a pharmaceutically-acceptable cation or ester group). The phosphonates herein are organophosphonates, i.e., the phosphonate moiety is attached to a carbon atom by a carbon-phosphorus bond (C—P bond). The carbon atom, in turn, can be bonded to other hydrocarbyl groups, e.g., alkyl phosphonates, or to hydrogen atoms, e.g., methane phosphonates, halogen atoms, e.g., dichloromethanediphosphonates, or to mixed hydrocarbyl groups, hydrogen atoms or other substituents, e.g., haloalkyl phosphonates. The hydrocarbyl groups can be substituted or non-substituted alkyl (including cycloalkyl), aryl (including heteroaryl) and the like. Substituent groups on the alkyl or aryl hydrocarbyl moiety can be, for example, additional phosphonate moieties; halogens, especially chlorine, carboxyl; esterified carboxyl; hydroxyl; amino; amido; and the like. Preferred for use herein are organophosphonates having more than one C—PO$_3$M$_2$ group; diphosphonates, especially geminal diphosphonates characterized by the grouping

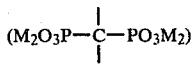

are most highly preferred.

Typical phosphonate compounds useful herein are of the formula

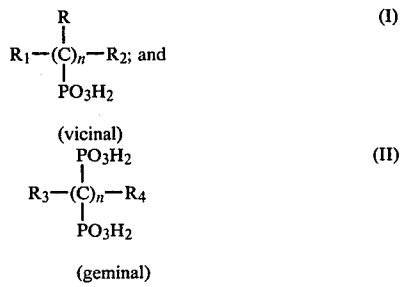

wherein n is an integer from 1 to about 10 and the substituent groups are H, alkyl, aryl, alkenyl, and the like. Examples of Type (I) phosphonates are those wherein R, R$_1$ and R$_2$ are each hydrogen, alkyl, —CH$_2$OH, or are as noted for groups R$_3$ and R$_4$. Examples of Type (II) phosphonates are those wherein R$_3$ is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., chlorine, bromine, and fluorine), amino, substituted amino (e.g., dimethylamino, diethylamino, N-hydroxy-N-ethylamino, acetylamino), —CH$_2$COOH, —CH$_2$PO$_3$H$_2$, —CH(PO$_3$H$_2$) (OH) or —CH$_2$CH(PO$_3$H$_2$)$_2$; R$_4$ is hydrogen, lower alkyl (e.g., methyl, ethyl, propyl, and butyl), amino, benzyl, halogen (e.g., chlorine, bromine and fluorine), hydroxyl, —CH$_2$COOH, —CH$_2$PO$_3$H$_2$, or —CH$_2$CH$_2$PO$_3$H$_2$, or a pharmaceutically-acceptable salt thereof such as alkali metal (e.g., sodium and potassium), alkaline earth metal (e.g., calcium and magnesium), non-toxic heavy metal (e.g., stannous and indium), and ammonium or low molecular weight substituted ammonium (e.g., mono-, di-, and tri-ethanolammonium) salts. It will be appreciated that groups R, R$_1$ and R$_2$ and groups R$_3$ and R$_4$ can be cycloalkyl, heterocyclic or can be joined in ring structures, said rings having carbocyclic or heterocyclic.

The above described organophosphonic acids and their pharmaceutically-acceptable salts and esters are commonly referred to collectively as "phosphonates", "diphosphonates" or "polyphosphonates".

Non-limiting examples of phosphonates of the above Type (I) include propane-1,2,3-triphosphonic acid; butane-1,2,3,4-tetraphosphonic acid; hexane-1,2,3,4,5,6-hexaphosphonic acid; hexane-1-hydroxy-2,3,4,5,6-pentaphosphonic acid; hexane-1,6-dihydroxy-2,3,4,5-tetraphosphonic acid; pentane-1,2,3,4,5-pentaphosphonic acid; heptane-1,2,3,4,5,6,7-heptaphosphonic acid; octane-1,2,3,4,5,6,7,8-octaphosphonic acid; nonane-1,2,3,4,5,6,7,8,9-nonaphosphonic acid; decane-1,2,3,4,5,6,7,8,9,10-decaphosphonic acid; and the pharmaceutically-acceptable salts of these acids, e.g., sodium, potassium, calcium, magnesium, ammonium, triethanolammonium, diethanolammonium, and monoethanolammonium salts.

Among the operable phosphonates encompassed by the above Type (II) are ethane-1-hydroxy-1,1-diphosphonic acid; methanediphosphonic acid; methanehydroxydiphosphonic acid; ethane-1,1,2-triphosphonic acid; propane-1,1,3-tetraphosphonic acid; ethane-2-phenyl-1,1-diphosphonic acid; ethane-2-nephthyl-1,1-diphosphonic acid; methanephenyldiphosphonic acid; ethane-1-amino-1,1-diphosphonic acid; dichloromethanediphosphonic acid (a.k.a. dichloromethylenediphosphonic acid and methanedichlorodiphosphonic acid); nonane-5,5-diphosphonic acid; n-pentane-1,1-diphosphonic acid; methanedifluorodiphosphonic acid; methanedibromodiphosphonic acid; propane-2,2-diphosphonic acid; ethane-2-carboxy-1,1-diphosphonic acid; propane-1-hydroxy-1,1,3-triphosphonic acid; ethane-2-hydroxy-1,1,2-triphosphonic acid; ethane-1-hydroxy-1,1,2-triphosphonic acid; propane-1,3-diphenyl-2,2-diphosphonic acid; nonane-1,1,-diphosphonic acid; hexadecane-1,1,-diphosphonic acid; pent-4-ene-1-hydroxy-1,1-diphosphonic acid; octadec-9-ene-1-hydroxy-1,1-diphosphonic acid; 3-phenyl-1,1,-diphosphonoprop-2-ene; octane-1,1-diphosphonic acid, dodecane-1,1-diphosphonic acid; phenylaminomethanediphosphonic acid; nephthylaminomethanediphosphonic acid; N,N-dimethylaminomethanediphosphonic acid; N-(2-hydroxyethyl)-aminomethanediphosphonic acid; N-acetylaminomethanediphosphonic acid; aminomethanediphosphonic acid; and the pharmaceutically-acceptable salts of these acids, e.g., sodium, potassium, calcium, magnesium, stannous, indium, ammonium, triethanolammonium, diethanolammonium, and monoethanolammonium salts.

Mixtures of any of the foregoing phosphonic acids and/or salts can be used in the practice of this invention.

The geminal diphosphonates of Type (II) are most preferred for use herein.

Ethane-1-hydroxy-1,1-diphosphonic acid is a preferred geminal diphosphonate for use herein. This compound has the molecular formula CH$_3$C(OH)(PO$_3$H$_2$)$_2$ (according to nomenclature by radicals, the acid may also be named 1-hydroxyethylidene diphosphonic acid). The most readily crystallizable salt of this acid is obtained when two or three of the acid hydrogens are replaced by sodium. Preferred salts for the purpose of this invention are the trisodium hydrogen salt and the disodium dihydrogen salt, and/or mixtures thereof.

Dichloromethanediphosphonic acid is an especially preferred geminal diphosphonate for use herein. This compound has the molecular formula Cl$_2$C(PO$_3$H$_2$)$_2$, abbreviated Cl$_2$MDP. The dichloromethanediphosphonates, especially the sodium salts of Cl$_2$MDP, are readily prepared and are most preferred for use in the practice of this invention.

The preparation of typical phosphonate compounds of the type disclosed for use herein is found in standard references and publications, especially the following.

Methanehydroxydiphosphonic acid and related compounds operable herein can be prepared, for example, by the reaction of phosgene with an alkali metal dialkylphosphite. A complete description of these compounds and the method for preparing same is found in U.S. Pat. No. 3,422,137, O. T. Quimby, incorporated herein by reference.

Ethane-1-hydroxy-1,1-diphosphonic acid can be prepared as disclosed in U.S. Pat. No. 3,400,149, incorporated herein by reference.

Methanediphosphonic acid and related compounds useful herein are described in detail in U.S. Pat. No. 2,213,030, granted Oct. 19, 1965; a preferred method of preparing such compounds is disclosed in U.S. Pat. No. 3,251,907, granted May 17, 1966, incorporated herein by reference.

Ethane-1,1,2-triphosphonic acid and related compounds which can be used in this invention, as well as a method for their preparation, are fully described in U.S. Pat. No. 3,551,339, O. T. Quimby, incorporated herein by reference.

Propane-1,1,3,3-tetraphosphonic acid and related compounds useful herein, and a method for preparing same are fully disclosed in U.S. Pat. No. 3,400,176, O. T. Quimby, incorporated herein by reference.

Pentane-2,2-diphosphonic acid and related compounds can be prepared in accordance with the method described by G. M. Kosolopoff in *J. Amer. Chem. Soc.* 75, 1500 (1953), incorporated herein by reference.

Propane-1,2,3-triphosphonic acid and salts thereof can be prepared by a process disclosed in U.S. Pat. No. 3,743,688, D. Allan Nicholson and Darrel Campbell, incorporated herein by reference.

Butane-1,2,3,4-tetraphosphonic acid and salts thereof can be prepared by a process disclosed in U.S. Pat. No. 3,755,504, D. Allan Nicholson and Darrel Campbell, incorporated herein by reference.

The higher aliphatic vicinal polyphosphonates and salts thereof can be prepared by the process disclosed in U.S. Pat. No. 3,584,035, Nicholson and Campbell, incorporated herein by reference.

Substituted ethane diphosphonic acids and salts and esters thereof are disclosed in U.S. Pat. No. 3,940,436, issued Feb. 24, 1976, to A. F. Kerst, the disclosures of which are incorporated herein by reference. U.S. Pat. No. 3,944,599, to the same inventor, discloses geminal diphosphonate compounds having halogen and hydroxyl substituent groups, and the means for preparing same. The disclosures of this patent are also incorporated herein by reference.

Phosphonobutane tri- and tetra-carboxylic acid compounds and their preparation are disclosed in U.S. Pat. Nos. 3,886,204 and 3,886,205, both issued May 27, 1975, to Geffers, et al., the disclosures of which are incorporated herein by reference.

German 2360-798, June 26, 1975, to Henkel & Cie GmbH discloses pharmaceutical and cosmetic preparations for influencing the deposition of poorly soluble calcium salts, said preparations comprising polymethylene phosphonic acid compounds. This publication, the disclosures of which are incorporated herein by reference, describes the preparation of the phosphonate materials in detail.

The preparation and pharmacological properties of various amino phosphonate compounds are described in German 2343-146 (March 6, 1975); Belgian 822-930 (June 4, 1975); Belgian 822,929 (Dec. 6, 1973); German 2360-711 (June 12, 1975); German 2360-719 (June 6, 1975); Belgian 819-187 (Feb. 26, 1975); Belgian 819-188 (Feb. 26, 1975); and Belgian 819-189 (Feb. 26, 1975), the disclosures of said publications being incorporated herein by reference.

While any pharmaceutically-acceptable salt of the phosphonates can be used in the practice of this invention, the sodium salts are preferred. Various pharmaceutical cations such as potassium, ammonium, mono-, di-, and tri-ethanolammonium, and mixtures thereof, are also suitable for use as counterions in the salts, provided caution is observed in regulating the total intake of cation species in the salt composition. Such salts can be prepared by any suitable method involving neutralization of the parent phosphonic acid.

As can be seen from the foregoing, the preparation of the phosphonates used in the practice of this invention can be accomplished using well-known methods, or by simple modificatons of various art-disclosed procedures. Only those organophosphonates which are pharmaceutically acceptable (i.e., provide a satisfactory benefit:risk ratio) are contemplated for use herein. The well-known toxicity of some Type (I) monophosphonates (n=1) disclosed in the structural formulas above precludes their use herein. However, such materials are known in the art and are easily avoided in the practice of this invention.

The present invention is most conveniently practiced by administering compositions which comprise mixtures of the indole-based anti-inflammatory agent and the phosphonate agent. In an alternate mode, a dosage regimen can consist of separate administration of the two types of agents, but this is less convenient.

Compositions comprising the indole-based anti-inflammatory agent and the phosphonate compound can be administered parenterally in aqueous solution by subcutaneous, intradermal, intramuscular or intravenous injection.

When administered orally, the phosphonate compounds herein are only about 10% absorbed through the gut, the rest being excreted. Accordingly, oral compositions typically contain an excess of the phosphonate material over that which can be effectively used in an injectable form to account for the low absorption.

Especially useful compositions herein for oral administration comprise, in unit dosage form, from about 10 mg to about 500 mg of indomethacin (preferred) or indoxole and from about 50 mg to about 250 mg of dichloromethanediphosphonic acid, or a pharmaceutically-acceptable salt thereof. Similarly, oral compositions in unit dosage form comprising from about 10 mg to about 500 mg of indomethacin or indoxole and from about 50 mg to about 250 mg of ethane-1-hydroxy-1,1-diphosphonic acid, or a pharmaceutically-acceptable salt thereof, or methanediphosphonic acid, or a pharmaceutically-acceptable salt thereof, are useful in the practice of the invention.

Of course, the total daily usage of the compositions herein will be decided by the attending physician and will be determined by such factors as the type of inflammation being treated, the age and weight of the patient, the severity of the inflammation, and like factors well known in the medical arts. In general, treatment regimens according to the present invention comprise administering to an animal in need of such treatment from about 50 mg to about 6000 mg (preferably 100-1000 mg) of indole-based compound per day and from about 200 mg to about 2000 mg per day of the diphosphonates herein, especially dichloromethanediphosphonic acid, ethane-1-hydroxy-1,1-diphosphonic acid, methanediphosphonic acid, or the pharmaceutically-acceptable salts or esters of these respective acids; the dichloromethanediphosphonates are particularly useful herein due to their safety and efficacy.

For purposes of oral administration, compositions can be formulated as capsules, tablets or granules. For treatment of non-human animals, compositions are preferably incorporated in animal feeds, feed supplements or feed concentrates.

Compositions comprising the indole-based anti-inflammatory agent and phosphonate can be administered, per se, or, more preferably, in combination with a solid or liquid filler, diluent or encapsulating substance as a pharmaceutical carrier, e.g., materials commonly used in the manufacture of tablets, capsules, elixirs, and the like. Some examples of the substances which can serve as pharmaceutical carriers herein include pyrogen-free water; water-alcohol mixtures; saline; sugars such as lactose, glucose and sucrose; starches such as corn starch and potato starch; cellulose and its derivatives, such as sodium carboxymethylcellulose, ethylcellulose, cellulose acetate; powdered gums; malt; gelatin; stearic acid; calcium sulfate; vegetable oils, such as peanut oil and cottonseed oil; mineral oil; polyols such as propylene glycol, glycerin, sorbitol, mannitol and polyethylene glycol; agar; alginic acid; as well as other non-toxic, compatible substances used in pharmaceutical formulations. Wetting agents and lubricants such as sodium lauryl sulfate, as well as coloring agents, flavoring agents and preservatives can also be present.

For topical application directly to the afflicted situs, the compositions herein are preferably formulated as solutions in a liquid or semi-liquid carrier. Carriers which promote penetration of the present compositions into and through the skin to the subdermal, inflamed tissues are preferred in such topical compositions. The organic sulfoxides and phosphine oxides and mixtures thereof with sugar esters, and liquid and semi-liquid carriers comprising same, which are preferred for use with the present compositions, are fully described in U.S. Pat. Nos. 3,903,256 and 3,839,566, MacMillan and Lyness, and U.S. Pat. Nos. 3,896,238 and 3,952,099, Smith, the disclosures of which are incorporated herein by reference.

Topical compositions herein generally comprise from about 1% to 20% of the indole-based compound, from about 1% to about 20% of the phosphonate compound, the balance comprising a compatible carrier, usually a liquid or cream. Especially effective carriers comprise a $C_{10}$, or higher, organic sulfoxide compound to enhance skin penetration by the active drug agents. Decyl methyl sulfoxide (0.1%-10% of the topical composition) is especially useful for enhancing penetration of the drug agents through skin.

The compositions herein can be prepared by standard formulation and tableting techniques used in the pharmaceutical industry.

The following examples illustrate the present compositions and their use, but are not intended to be limiting of the scope of the invention.

EXAMPLE I

Capsules are prepared by conventional methods, as follows:

| Ingredient | mq. per capsule |
| --- | --- |
| Ethane-1-hydroxy-1,1-diphosphonic acid | 200 |
| Indomethacin | 25 |

A capsule of the above type is administered orally 2-4 times daily to substantially reduce the pain and inflammation associated with arthritis, rheumatism, bursitis and lumbago.

In the composition of Example I, the ethane-1-hydroxy-1,1-diphosphonic acid is replaced by ethane-1-hydroxy-1,1-diphosphonic acid, sodium salt form, and equivalent results are secured.

In the capsules of Example I, the indomethacin is replaced by an equivalent amount of indoxole, and equivalent results are secured.

EXAMPLE II

Capsules are prepared by conventional methods, as follows:

| Ingredient | mg. per capsule |
| --- | --- |
| Dichloromethanediphosphonic acid | 200 |
| Indomethacin | 25 |

A capsule of the above type is administered orally 2-4 times daily to substantially reduce the pain and inflammation associated with arthritis, rheumatism, bursitis and lumbago.

In the composition of Example II, the dichloromethanediphosphonic acid is replaced by dichloromethanediphosphonic acid, sodium salt form, and equivalent results are secured.

In the capsules of Example II, the indomethacin is replaced by an equivalent amount of indoxole and equivalent results are secured.

EXAMPLE III

A topical composition is prepared by blending the following ingredients:

| Ingredient | % by Wt. |
| --- | --- |
| Decyl methyl sulfoxide | 0.5 |
| Ethane-1-hydroxy-1,1-diphosphonic acid, disodium salt | 5.0 |
| Indomethacin | 10.0 |
| Water | Balance |

The composition of Example III is applied topically to the joints of animals and humans to reduce pathological calcification associated with arthritis-like conditions caused by stress at the joints.

In the composition of Example III, the diphosphonate material is replaced by an equivalent amount of dichloromethanediphosphonic acid, disodium salt, and equivalent results are secured.

In the topical composition of Example III, the indomethacin is replaced by an equivalent amount of indoxole and equivalent results are secured.

EXAMPLE IV

A suppository suitable for human or animal use is prepared from the following ingredients:

| Ingredient | % by Wt. |
|---|---|
| Indomethacin | 10.0 |
| Dichloromethanediphosphonic acid, disodium salt | 10.0 |
| Cocoa butter | Balance |

The composition of Example IV is prepared by melting the cocoa butter at a temperature of ca. 39° C. and adding the diphosphonate and indomethacin materials to the melt, with blending, to provide a homogeneous system. The cocoa butter/phosphonate/indomethacin melt is poured into molds of appropriate dimensions and allowed to solidify. The resulting product is a lubricious suppository, or the like, which melts at body temperature to release the phosphonate and indomethacin drug agents to provide improved anti-inflammatory benefits.

An injectable composition is prepared by replacing the cocoa butter of Example IV with sterile, pyrogen-free water.

What is claimed is:

1. A method for treating or preventing pain and inflammation in animal tissues, comprising administering to an animal in need of such treatment from about 50 milligrams to about 6000 milligrams per day of an indole-based anti-inflammatory compound selected from indomethacin and pharmaceutically acceptable salts and esters thereof and from about 200 milligrams to about 2000 milligrams per day of an organophosphonate compound selected from the group consisting of geminal organophosphonates of the formula

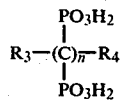

or pharmaceutically acceptable salts thereof, wherein n is an integer from 1 to about 10; $R_3$ is selected from the group consisting of H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$C_2PO_3H_2$, —$CH(PO_3H_2)$ (OH) or —$CH_2CH(PO_3H_2)_2$; and $R_4$ is selected from the group consisting of H, lower alkyl, amino, benzyl, halogen, —OH, —$CH_2COOH$, —$CH_2PO_3H_2$, or —$CH_2CH_2PO_3H_2$.

2. A method according to claim 1 wherein the organophosphonate compound is a member selected from the group consisting of ethane-1-hydroxy-1,1-diphosphonic acid, and the pharmaceutically-acceptable salts thereof; dichloromethanediphosphonic acid, and the pharmaceutically-acceptable salts thereof; and methanediphosphonic acid, and the pharmaceutically-acceptable salts thereof.

3. A method according to claim 2 wherein the animal is a human.

4. A method according to claim 3 which employs a safe and effective amount of indomethacin and a safe and effective amount of dichloromethanediphosphonic acid, or the pharmaceutically-acceptable salts or esters thereof.

5. A method according to claim 3 which employs a safe and effective amount of indomethacin and a safe and effective amount of ethane-1-hydroxy-1,1-diphosphonic acid, or the pharmaceutically-acceptable salts or esters thereof.

6. A method according to claim 3 which employs a safe and effective amount of indomethacin and a safe and effective amount of methanediphosphonic acid, or the pharmaceutically-acceptable salts or esters thereof.

7. A composition of matter for treating pain and inflammation in animal tissue, comprising from about 10 milligrams to about 500 milligrams of an indole-based anti-inflammatory compound selected from indomethacin and pharmaceutically acceptable salts and esters thereof and from about 50 milligrams to about 250 milligrams of an organophosphonate compound selected from the group consisting of geminal organophosphonates of the formula

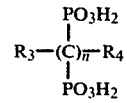

or pharmaceutically acceptable salts thereof, wherein n is an integer from 1 to about 10; $R_3$ is selected from the group consisting of H, $C_1$–$C_{20}$ alkyl or cycloalkyl, $C_2$–$C_{20}$ alkenyl, aryl, phenylethyl, benzyl, halogen, amino, substituted amino, —$CH_2COOH$, —$CH_2PO_3H_2$, —$CH(PO_3H_2)$ (OH) or —$CH_2CH(PO_3H_2)_2$; and $R_4$ is selected from the group consisting of H, lower alkyl, amino, benzyl, halogen, —OH, —$CH_2COOH$, —$CH_2PO_3H_2$, or —$CH_2CH_2PO_3H_2$.

8. A composition according to claim 7 wherein the organophosphonate compound is a member selected from the group consisting of ethane-1-hydroxy-1,1-diphosphonic acid, and the pharmaceutically-acceptable salts thereof; dichloromethanediphosphonic acid, and the pharmaceutically-acceptable salts thereof; and methanediphosphonic acid, and the pharmaceutically-acceptable salts thereof.

9. A composition according to claim 7, comprising a safe and effective amount of indomethacin and a safe and effective amount of dichloromethanediphosphonic acid, or the pharmaceutically-acceptable salts or esters thereof.

10. A composition according to claim 7, comprising a safe and effective amount of indomethacin and a safe and effective amount of methanediphosphonic acid, or the pharmaceutically-acceptable salts or esters thereof.

* * * * *

UNITED STATES PATENT AND TRADEMARK OFFICE
CERTIFICATE OF CORRECTION

PATENT NO. : 4,269,828

DATED : May 26, 1981

INVENTOR(S) : Lawrence Flora and Marion D. Francis

It is certified that error appears in the above-identified patent and that said Letters Patent are hereby corrected as shown below:

Column 2, line 64, "infole-based" should read "indole-based".

Column 7, line 21, "2,213,030" should read "3,213,030".

Please add the following claim.

11. A composition according to Claim 7, comprising a safe and effective amount of indomethacin and a safe and effective amount of ethane-1-hydroxy-1,1-diphosphonic acid, or the pharmaceutically-acceptable salts or esters thereof.

On the title page, after the "Abstract", "10 Claims" should read --- 11 Claims ---.

Signed and Sealed this

Twenty-eighth Day of July 1981

[SEAL]

Attest:

GERALD J. MOSSINGHOFF

Attesting Officer

Commissioner of Patents and Trademarks